United States Patent [19]

Morini et al.

[11] Patent Number: 5,552,359

[45] Date of Patent: Sep. 3, 1996

[54] COMPONENTS AND CATALYST FOR THE POLYMERIZATION OF OLEFINS

[75] Inventors: Giampiero Morini, Pavia; Luisa Barino, Novara; Raimondo Scordamaglia, Milan; Elisabetta Barbassa, Pavia; Giovanni Baruzzi, Ferrara, all of Italy

[73] Assignee: Montell North America Inc., Wilmington, Del.

[21] Appl. No.: 391,327

[22] Filed: Feb. 21, 1995

Related U.S. Application Data

[63] Continuation of Ser. No. 125,947, Sep. 23, 1993, abandoned.

[30] Foreign Application Priority Data

Sep. 24, 1992 [IT] Italy .................. MI92A2197

[51] Int. Cl.$^6$ .................................. B01J 31/00
[52] U.S. Cl. ................. 502/123; 502/115; 502/118; 502/104; 502/110
[58] Field of Search .................. 502/115, 118, 502/123, 104, 110

[56] References Cited

U.S. PATENT DOCUMENTS

| | | | |
|---|---|---|---|
| 3,219,651 | 11/1965 | Hill et al. .................. | 502/123 |
| 4,107,414 | 8/1978 | Giannini et al. .......... | 526/114 |
| 4,186,107 | 1/1980 | Wagner ..................... | 502/110 |
| 4,277,372 | 7/1981 | Matlack ..................... | 502/104 |
| 4,298,718 | 11/1981 | Mayr et al. ............... | 526/125 |
| 4,343,721 | 8/1982 | Goodall et al. ........... | 502/123 |
| 4,465,782 | 8/1984 | McKenzie .................. | 502/104 |
| 4,487,845 | 12/1984 | Triplett ..................... | 502/123 |
| 4,506,029 | 3/1985 | Band ......................... | 502/104 |
| 4,522,930 | 6/1985 | Albizzati et al. ......... | 502/124 |
| 4,532,313 | 7/1985 | Matlack ..................... | 502/104 |
| 4,544,717 | 10/1985 | Mayr et al. ............... | 526/125 |
| 5,068,213 | 11/1991 | Albizzati et al. ......... | 502/126 |

FOREIGN PATENT DOCUMENTS

| | | |
|---|---|---|
| 0086645 | 8/1923 | European Pat. Off. . |
| 0045977 | 2/1982 | European Pat. Off. . |
| 2135584 | 2/1972 | Germany . |
| 47-051831 | 12/1972 | Japan . |
| 2054616 | 2/1981 | United Kingdom . |

OTHER PUBLICATIONS

Jutz et al., "Reaction of Vinylogous Formamidinium Salts with Nucleophiles . . .", 1977, (Chem. Abstracts). (no month).

Jack Hine et al., "Synthesis of Some cis- and trans-2-Dimethylaminomethyl Cyclic Amines and Related Diamines", Journal of Organic Chemistry, vol. 40, No. 3, pp. 289–291, (1975). (no month).

Gansser et al., "N–Substitued ortho-toluidine derivatives", Eur. J. Med. Chem., 12(4), (abstract) 1977 (no month).

*Primary Examiner*—Asok Pal
*Assistant Examiner*—Walter D. Griffin

[57] ABSTRACT

Disclosed are catalyst components for the polymerization of olefins which include magnesium halide in active form, and, supported thereon, a titanium halide or titanium halogen alcoholate and an electron-donor compound selected from the group diamines of formula

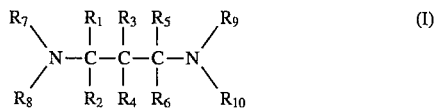

wherein the radicals $R_1$ to $R_{10}$ are the same or different and are hydrogen or $C_1$–$C_{18}$ hydrocarbon radicals, with the proviso that at least one of the $R_7$ and $R_8$ radicals and at least one of the $R_9$ and $R_{10}$ radicals are not hydrogen. Also, disclosed are catalysts obtained from the catalyst components and an Al-alkyl compound, as well as catalysts obtained by reaction of an Al-alkyl compound and a diamine of formula (I) with a solid catalyst component including a titanium halide or a titanium halogen alcoholate, and an electron-donor compound having particular characteristics of extractability with Al-triethyl, supported on magnesium halide in active form.

9 Claims, No Drawings

COMPONENTS AND CATALYST FOR THE POLYMERIZATION OF OLEFINS

This application is a continuation of application Ser. No. 08/125,947, filed Sep. 23, 1993, now abandoned.

BACKGROUND OF THE INVENTION

The present invention relates to components and catalysts for the polymerization of olefins, as well as to specific diamines which can be used as electron donors in said catalysts.

Catalysts comprising titanium compounds supported on magnesium halides in active form are well known in the art. Catalysts of this type are described in U.S. Pat. No. 4,298,718, for example.

Although highly active both in the polymerization of the ethylene and α-olefins, such as propylene, said catalysts are not sufficiently stereospecific.

Stereospecificity has been improved by adding an electron-donor compound to the solid component comprising the titanium compound (U.S. Pat. No. 4,544,717).

Further improvements have been obtained by using both an electron-donor compound added to the solid component (internal donor) and one added to the Al-alkyl compound (external donor) (U.S. Pat. No. 4,107,414).

Very high performances, in terms of activity as well as stereospecificity, are given by the catalysts described in European patent no. 0045977. Said catalysts comprise an magnesium halide in active form as the solid component, on which is supported a titanium halide (TiCl$_4$) and an electron-donor compound selected from specific classes of carboxylic acid esters, such as phthalates for example. The co-catalyst used is an Al-alkyl compound to which is added a silicon compound containing at least one Si-OR bond (R=hydrocarbon radical).

U.S. Pat. No. 4,522,930 describes catalysts whose solid catalyst component is characterized in that it contains an electron-donor compound which can be extracted by means of Al-triethyl (under standard extraction conditions) for at least 70% in moles and in that it has a surface area of at least 20 m$^2$/g after extraction.

Said catalysts comprise an Al-trialkyl compound as cocatalyst, to which is added an electron-donor compound (external donor) having the property of not causing complexing reactions with Al-triethyl, which reactions are detectable by potentiometric titration under well defined reaction conditions. The above mentioned electron-donor compounds comprise silicon compounds having Si—OR bonds; 2,2,6,6-tetramethylpiperidine, 2,2,5,5-tetramethylpyrrolidine, Al-diethyl- 2,2,6,6-tetramethylpiperidide, Al-dichloromonophenoxy and other compounds.

Unexpectedly a new class of amines has now been found that are useful in the formation of catalysts and catalyst components for the polymerization of olefins. Namely, the amines of the invention have the property of providing highly active and stereospecific catalysts when used as internal donors, i.e. when they are present in solid catalyst components comprising a titanium halide, or a titanium halogen alcoholate, supported on magnesium halide in active form. The co-catalyst used is an Al-alkyl compound, optionally in combination with an electron-donor compound (external donor).

The above result is particularly surprising if one considers the fact that there are no known amines capable of giving good performances when used as internal donors.

Even when used as external donors, i.e. in combination with Al-alkyl compounds and solid catalyst components having the characteristics described in U.S. Pat. No. 4,522,930, the amines of the invention form highly active and stereospecific catalysts.

SUMMARY OF THE INVENTION

Accordingly the present invention provides a catalyst component for the polymerization of olefins comprising a magnesium halide in active form and, supported thereon, a titanium halide or a titanium halogen alcoholate and a diamine of formula

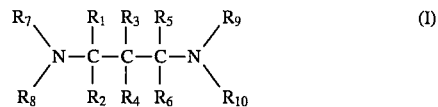

wherein the radicals $R_1$ to $R_{10}$ are the same or different, and are hydrogen or $C_1$–$C_{18}$ linear or branched alkyl radicals, $C_3$–$C_{18}$ cycloalkyl radical, $C_6$–$C_{18}$ aryl radicals, $C_7C_{18}$ alkaryl or aralkyl radicals, with the proviso that at least one of the $R_7$ and $R_8$ radicals and at least one of the $R_9$ and $R_{10}$ radicals are not hydrogen.

According to another embodiment, the present invention provides a catalyst for the polymerization of olefins comprising the reaction product of:

A) a catalyst component as defined above;
B) an Al-alkyl compound; and optionally
C) an electron donor compound.

According to another embodiment, the present invention provides a catalyst for the polymerization of olefins comprising the product of the reaction of an Al-alkyl compound and a diamine of formula (I) with a solid component comprising a magnesium halide in active form, a titanium halide or titanium halogen alcoholate, and an electron-donor compound extractable with Al-triethyl for at least 70% in moles under standard extraction conditions, said solid component having a surface area greater than 20 m$^2$/g after extraction.

According to a further embodiment, the present invention provides the diamines of formula (I).

DESCRIPTION OF THE PREFERRED EMBODIMENTS

Preferably the $R_1$ to $R_6$ radicals are selected from hydrogen, methyl, ethyl, n-propyl, isopropyl, n-butyl, isobutyl, sec-butyl, tert-butyl, cyclohexyl, cyclohexenyl, cyclohexylmethyl, phenyl and benzyl. The $R_7$ to $R_{10}$ radicals are preferably different from hydrogen, more preferably they are selected from $C_1$–$C_6$ alkyl and $C_3$–$C_6$ cycloalkyls; in particular, they are methyls. Specific examples of diamines of formula (I) are: 1,3-bis(dimethylamino)propane; 1,3 -bis(dimethylamino)-2-methylpropane; 1,3-bis(dimethylamino)-2 -ethylpropane;
1,3-bis(dimethylamino)-2-isopropylpropane;
1,3-bis(dimethylamino)-2-n-butylpropane;
1,3-bis(dimethylamino)-2-isobutylpropane;
1,3-bis(dimethylamino)-2-tert-butylpropane;
1,3-bis(dimethylamino)-2-cyclohexylpropane;
1,3-bis(dimethylamino)-2-phenylpropane;
1,3-bis(dimethylamino)-2,2-dimethylpropane;
1,3-bis(dimethylamino)-2-methyl-2-ethylpropane;
1,3-bis(dimethylamino)-2-methyl-2-n-propylpropane;
1,3-bis(dimethylamino)-2-methyl-2-sec-butylpropane;
1,3-bis(dimethylamino)-2,2-diethylpropane;

1,3-bis(dimethylamino)-2-ethyl-2-n-butylpropane;
1,3-bis(dimethylamino)-2,2-dibenzylpropane;
1,3-bis(dimethylamino)-2,2-diphenylpropane;
1,3-bis(dimethylamino)-2,2-dicyclohexylpropane;
1,3-bis(dimethylamino)-1-methylpropane
1,3-bis(dimethylamino)-1-phenylpropane;
1,3-bis(dimethylamino)-1,2-dimethylpropane;
1,3-bis(dimethylamino)-1-ethyl-2-methylpropane;
1,3-bis(dimethylamino)-1-methyl-2-tert-butylpropane;
1,3-bis(dimethylamino)-1,2,2-trimethylpropane;
1,3-bis(dimethylamino)-1-isopropyl-2,2-dimethylpropane;
1,3-bis(dimethylamino)-2-cyclohexyl-2(1-cyclohexenyl)-propane.

Other specific examples of diamines of formula (I) are the compounds having the same structure as the ones listed above, but with methylethylamino, diethylamino, methylpropylamino, ethylpropylamino, or dipropylamino groups instead of the dimethylamino groups.

The diamines of formula (I) can be prepared in various ways. One method, for example, consists of reacting an aldehyde or a ketone with formaldehyde and dimethylamine by the Mannich reaction in order to form the corresponding amino-aldehyde or amino-ketone. The reaction intermediate is reacted with hydroxylamine hydrochloride to form the oxime, which in turn is reduced with $LiAlH_4$ to produce the corresponding 3-(N,N-dimethyl-amino)-propanamine. The latter is methylated in the presence of formaldehyde and acetic acid to form the corresponding formula (I) tertiary 1,3-diamine.

The preparation of the catalyst components containing the amines of formula (I) is carried out according to various methods.

As a way of example, the magnesium halide (used in the anhydrous state containing less than 1% by weight water), the titanium compound and the diamine are milled together under conditions that cause the magnesium halide to be activated; the milled product is then treated one or more times with $TiCl_4$ in excess at a temperature ranging from 80° C. to 135° C., and then washed repeatedly with a hydrocarbon (e.g. hexane) until all chlorine ions have disappeared.

According to another method, anhydrous magnesium halide is pre-activated according to known methods and then reacted with an excess $TiCl_4$ containing the diamine in solution. Also in this case the temperature is 80° to 135° C. The treatment with $TiCl_4$ is optionally repeated and the solid is then washed with hexane or heptane to eliminate traces of unreacted $TiCl_4$.

According to another method, a $MgCl_2 \cdot nROH$ (in particular in the form of spheroidal particles) where n is generally from 1 to 3 and ROH is an alcohol e.g. ethanol, butanol, isobutanol, is reacted with an excess $TiCl_4$ containing the diamine in solution. The temperature is generally from 80° to 120° C. After the reaction, the solid is reacted once again with $TiCl_4$, separated and washed with a hydrocarbon until chlorine ions have disappeared.

According to a further method, magnesium alcoholates and magnesium chloroalcoholates (the chloroalcoholates can be prepared in particular according to U.S. Pat. No. 4,220,554) are reacted with an excess $TiCl_4$ containing the diamine in solution, also in this case by operating in the conditions described above.

According to another method, magnesium halide/titanium alcoholate complexes such as the $MgCl_2 \cdot 2Ti(OC_4H_9)_4$ complex, for example, are reacted, in hydrocarbon solution, with the excess $TiCl_4$ containing the diamine in solution; the solid product which is separated is then further reacted with an excess of $TiCl_4$, and then separated and washed with hexane.

The reaction with $TiCl_4$ is carried out at a temperature from 80° to 120° C.

According to a variation, the $MgCl_2$/titanium alcoholate complex is reacted, in hydrocarbon solution, with methyl-hydropolysiloxane; the solid product is separated and reacted at 50° C. with silicon tetrachloride containing the diamine in solution; said solid is then reacted with the $TiCl_4$ in excess operating at 80°–120° C.

Finally, one can react with the excess $TiCl_4$ containing the diamine in solution, porous resins, such as partially cross-linked styrene-divinylbenzene resins in the form of spheroids, or porous inorganic oxides, such as silica and alumina, impregnated with solutions of Mg compounds or complexes soluble in organic solvents. The porous resins that can be used are described in published European patent application 344755.

The reaction with $TiCl_4$ is carried out at 80°–120° C.; after the excess $TiCl_4$ is-separated, the reaction is repeated, and the solid is then washed with a hydrocarbon.

The molar ratio between the magnesium chloride and the diamine used in the above mentioned reactions ranges generally from 2:1 to 12:1. Generally speaking, the diamine is fixed on the magnesium halide in quantities ranging from 5 to 20% molar.

However, in the case of components supported on resins and inorganic oxides, the molar ratio between the amine and the magnesium is different and ranges generally from 0.1 and 1.

The Mg/Ti ratio in the catalyst components is generally from 30:1 to 4:1; in the components supported on resin or inorganic oxides, the ratio is different and generally is from 20:1 to 2:1.

The titanium compounds that can be used for the preparation of the catalyst components are halides and halogen alcoholates. The titanium tetrachloride is the preferred compound.

Satisfactory results are obtained also with titanium trihalides, particularly $TiCl_3$ HR, $TiCl_3$ ARA, and with halogen alcoholates such as $TiCl_3OR$ wherein R is a phenyl radical.

The above mentioned reactions bring to the formation of magnesium halide in active form. Reactions which bring to the formation of magnesium halide in active form starting from magnesium compounds different from the halides are well known in literature.

The active form of the magnesium halides in catalyst components is recognizable in that the X-ray diffraction spectrum of the catalyst component no longer shows the major intensity reflection which appears in the spectrum of the unactivated magnesium halides (having a surface area smaller than 3 $m^2/g$), but in its place there is a halo with the maximum intensity shifted with respect to the position of the major intensity reflection, or by the fact that the intensity of the major intensity reflection has diminished, and the major intensity reflection presents a mid-peak width at least 30% greater that the one of the major intensity reflection which appears in the spectrum of the unactivated Mg halide.

The most active forms of magnesium halide are those in which the halo appears in the X-ray spectrum of the solid catalyst component.

Among the magnesium halides, the chloride is the preferred compound. In case of the most active forms of the magnesium chloride, in the X-ray spectrum of the catalyst component appears a halo in place of the reflection which in the chloride spectrum is situated at the interplanar distance of 2.56 Å.

The solid catalyst components containing the diamines of formula (I) form, by reaction with Al-alkyl compounds, catalysts which can be used in the polymerization of $CH_2=CHR$ olefins, wherein R is hydrogen or a 1–8 carbon alkyl radical or an aryl, in the polymerization of mixtures of said olefins and in the polymerization of mixtures of said olefins with diolefins.

In particular, the Al-alkyl compounds that can be used are selected from Al-trialkyls, such as Al-triethyl, Al-triisobutyl and Al-tri-n-butyl, and linear or cyclic Al-alkyl compounds containing one or more Al atoms bonded between them by way of O or N atoms, or $SO_4$ and $SO_3$ groups.

Examples of said compounds are:

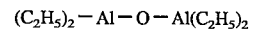

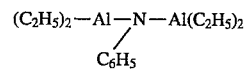

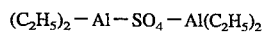

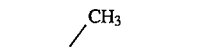

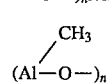

wherein n is a number from 1 to 20.

The Al-alkyl compound is used in Al/Ti ratios usually ranging from 1 to 1000.

In the case of the polymerization of propylene and higher α-olefins, the trialkyl compounds can be used in a mixture with Al-alkyl halides such as $AlEt_2Cl$ and $Al_2Et_3Cl_3$.

In the case of stereoregular polymerization of olefins, if an electron-donor compound is added to the Al-alkyl, the ratio between Al-Alkyl compound and electron-donor compound is usually between 5:1 and 100:1. Said electron-donor compound is preferably selected from the external donors described in U.S. Pat. No. 4,522,930. Particularly preferred are the electron-donors compounds of formula: $R_mSiY_nX_p$ wherein:

R is a $C_1$–$C_{20}$ alkyl, $C_2$–$C_{20}$ alkenyl, $C_6$–$C_{20}$ aryl, $C_7$–$C_{20}$ aralkyl or $C_3$–$C_{20}$ cycloalkyl;

Y is an —OR', -OCOR', —NR'$_2$ radical wherein R' is the same or different from R and has the same meaning as R;

X is a halogen or hydrogen atom or an —OCOR" or —NR"$_2$ group wherein R" is the same or different from R' and has the same meaning as R';

m is a number from 0 to 3, n is a number from 1 to 4, p is a number from 0 to 1; m+n+p is equal to 4.

Specific examples are: phenylalkoxysilanes, such as phenyltriethoxysilane or phenyltrimethoxysilane, diphenyldimethoxysilane and diphenyldiethoxysilane, and monochlorophenyldiethoxysilane; alkylalkoxysilanes, such as ethyltriethoxysilane and ethyltriisopropoxysilane.

As previously stated, the diamines of formula (I) can also be used as external donors, in combination with Al-alkyl compounds and solid components having the characteristics described in U.S. Pat. No. 4,522,930. The catalyst components described in said U.S. patent comprise a titanium compound containing a Ti-halide bond and an electron-donor compound extractable by at least 70% in moles with Al-triethyl under standard extraction conditions. After extraction, the solid has a surface area (B.E.T.) of at least 20 m$^2$/g, generally from 100 to 300 m$^2$/g.

The electron-donor compounds that can be used in the preparation of the catalyst components described in said U.S. patent comprise ethers, ketones, lactones, compounds containing N, P and/or S atoms, and specific types of esters. Besides the esters of U.S. Pat. No. 4,522,930, one can use also the classes of esters described in European patent 0045977.

Particularly adequate are the esters of phthalic acid, such as diisobutyl, dioctyl and diphenyl phthalate, benzylbutyl phthalate; malonic acid esters such as diisobutyl and diethyl malonate; alkyl and aryl pivalates; alkyl, cycloalkyl and aryl maleates; alkyl and aryl carbonates such as diisobutyl carbonate, ethylphenyl carbonate and diphenyl carbonate; esters of succinic acid such as the mono- and diethyl succinate. The phthalic acid esters are the preferred ones.

Generally speaking, the above catalyst components can be prepared with the methods described above using the above mentioned electron-donors instead of the diamines of formula (I).

The polymerization of olefins is carried out according to known methods operating in liquid phase consisting of the monomer or monomers, or of a solution of the same in a aliphatic or aromatic hydrocarbon solvent, or in gas phase, or combining liquid and gas phase techniques.

The (co-)polymerization temperature generally is from 0° to 150° C., generally from 60° to 100° C.; the operation is carried out at atmospheric pressure or higher.

The catalysts can be precontacted with small quantities of olefins (prepolymerization). Said prepolymerization improves both the performance of the catalysts and the morphology of the polymers.

The prepolymerization is carried out maintaining the catalyst in suspension in a hydrocarbon solvent (hexane, heptane, for example) and polymerizing at a temperature between room temperature and 60° C., until a quantity of polymer is produced which generally ranges from 0.5 to 3 time the weight of the catalyst. The operation can also occur in liquid propylene, under the temperature conditions mentioned above, thus producing quantities of polymer up to 1000 g per g of catalyst component.

The following examples are given to illustrate the invention without limiting the same.

EXAMPLE 1

Preparation of the 1,3-bis(dimethylamino)-2,2-dimethylpropane a) Preparation of 2,2-dimethyl-3-dimethylaminopropionaldehyde.

Into a 250 ml flask equipped with agitator, refrigeration device and thermometer are introduced:

34 g of isobutyraldehyde (0.47 moles) freshly distilled;

20 ml of absolute ethanol;

32 g of dimethylamine hydrochloride (0.39 moles);

18 g paraformaldehyde.

The content is heated in reflux for one hour. An additional 18 g of paraformaldehyde are introduced, and the content is heated in reflux for one more hour. The reaction mixture becomes more and more homogeneous, and at the end only a little solid residue of paraformaldehyde remains. The content is cooled, basified, and an oil which is distilled and has a boiling point=143°–144° C. is isolated. 42.4 g of 2,2-dimethyl-3-dimethylamino-propionaldehyde are recovered (yield=69.9%).

$^1$H-NMR (CDCl$_3$):

δ (in ppm):

1.1 (s, 6H, CH$_3$C)

2.15 (s, 6H, CH₃N)
2.4 (s, 2H, CH₂N)
9.5 (s, 1H, CHO)

b) Preparation of 2,2-dimethyl-3-dimethylaminopropylamine

A concentrated aqueous solution of 16.4 g of sodium carbonate (0.15 moles) is added dropwise to a mixture consisting of 40 g of 2,2-dimethyl-3-dimethylaminopropionaldehyde (0.31 moles) prepared above, and a saturated aqueous solution of hydroxylamine hydrochloride (0.34 moles).

After about one hour of agitation 21.3 g of oxime are obtained in the form of white crystals with a melt point= 52°–55° C. (yield=47.7%).

$^1$H-NMR (CDCl₃):
δ (in ppm):
1.10 (s, 6H, CH₃C)
2.28 (s, 6H, CH₃N)
2.30 (s, 2H, CH₂N)
7.37 (s, 1H, CH=N)

Into a 1 liter flask are introduced, in nitrogen atmosphere, 500 ml of anhydrous ethyl ether and 9.9 g of LiAlH₄ (0.26 moles).

18 g of oxime (0.125 moles) prepared above are then added slowly, and the content is heated in reflux for two days.

A 10% soda aqueous solution is added, thus forming a white precipitate which is removed by way of filtration.

The filtrate is distilled, and 9.2 g of 2,2-dimethyl-3-dimethylaminopropylamine with a boiling point=153° C. are obtained (yield=56.6%)

$^1$H-NMR (CDCl₃):
δ (in ppm):
0.83 (s, 6H, CH₃C)
1.13 (s, 2H, NH₂)
2.05 (s, 2H, CH₂N)
2.20 (s, 6H, CH₃N)
2.43 (s, 2H, CH₂NH₂)

c) Preparation of 1,3-bis(dimethylamino)-2,2-dimethylpropane.

Into a 100 ml flask equipped with agitator, refrigeration device, thermometer and drip funnel, are introduced 16.5 ml of acetic acid at 98%.

The reaction mixture is cooled, and 8 g of 2,2-dimethyl-3-dimethylaminopropylamine (0.061 moles) prepared above are slowly added dropwise. 19 ml of formaldehyde at 40% are added, and the content is heated in reflux for 15 hours, then cooled, acidified with 60 ml of HCl 4M, and dried. 35 ml of water and 35 ml of a NaOH 18M solution is added to the residue and an oil is separated. It is extracted with benzene (2 portions of 25 ml each) and anhydrated on K₂CO₃, after which it is distilled. The desired product boils at 70° C. at a pressure of 40 mm Hg and 5.8 ml are gathered (yield=60%).

$^1$H-NMR (CDCl₃):
δ (in ppm):
0.88 (s, 6H, CH₃O)
1.13 (s, 2H, NH₂)
2.12 (s, 4H, CH₂N)
2.27 (s, 12H, CH₃N)

Preparation of solid catalyst component 225 ml of TiCl₄ are introduced into a 500 ml reactor equipped with filtering barrier at 0° C. while under agitation, 10.3 g of microspheroidal MgCl₂.2,1C₂H₅OH, obtained as described below, are added over 15 minute. When the addition is completed the temperature is brought to 70° C., 9 mmoles of 1,3-bis(dimethylamino)-2,2-dimethylpropane are introduced, and the content is heated to 100° C., allowing it to react at this temperature for two hours, after which the TiCl₄ is filtered.

An additional 200 ml of TiCl₄ are introduced, and the content is allowed to react at 120° C. for one hour, after which it is filtered, and then washed at 60° C. with anhydrous heptane until all chlorine ions have disappeared from the filtrate.

The analysis of the solid component shows that it contains 14% by weight of Mg, 7% of Ti and 6.2% of diamine.

The microspheroidal MgCl₂.2,1C₂H₅OH adduct is prepared as follows. 48 g of anhydrous MgCl₂, 77 g of anhydrous C₂H₅OH, and 830 ml of kerosene are introduced, in inert gas and at ambient temperature, in a 2 liter autoclave equipped with turboagitator and dip-pipe. The content is heated to 120° C. while stirring, thus forming the adduct between MgCl₂ and the alcohol which melts and remains mixed with the dispersing medium. A nitrogen pressure is maintained inside the autoclave at 15 atm. The dip-pipe is heated externally to 120° C. with a heating jacket, has an inside diameter of 1 mm and is 3 meters long from one extremity of the heating jacket to the other.

The mixture is then made to flow through the pipe at a velocity of 7 m/sec.

At the output of the pipe the dispersion is collected in a 5 liter flask under agitation, said flask containing 2.5 liter of kerosene, cooled externally by a jacket maintained at the initial temperature of −40° C. The final temperature of the emulsion is 0° C.

The spherical solid product that constitutes the dispersed phase of the emulsion is separated by settling and filtering, after which it is washed with heptane and dried.

All these operations take place in an inert gas atmosphere.

130 g of MgCl₂.3C₂H₅OH in the form of solid spherical particles having a maximum diameter of less than 50 μm are obtained. The product thus obtained is then dealcoholated at temperatures gradually increasing from 50° C. to 100° C. in nitrogen atmosphere until the alcohol content reaches 2.1 moles per mole of MgCl₂.

Propylene Polymerization

Into a 4 liter stainless steel autoclave, equipped with anchor agitator and previously purged with nitrogen flow at 70° C. for one hour, are introduced, in propylene flow at 30° C., 80 ml of anhydrous n-hexane containing 20 mg of solid catalyst component, 7 mmoles of AlEt₃, and 1.4 mmoles of cyclohexylmethyldimethoxy-silane. The autoclave is closed, and 1.7 liters of hydrogen are introduced, the agitator is activated, and 1.2 kg of liquid propylene are added. The content is heated to 70° C. in 5 minutes and polymerized for two hours. At the conclusion of the polymerization the nonreacted propylene is removed and the polymer is recovered, dried in a 70° C. oven in nitrogen flow for 3 hours, after which it is characterized.

180 g of polymer are obtained (corresponding to a yield of 9000 g/gCat), said polymer having a fraction insoluble in xylene at 25° C. (X.I.) of 90%, and an intrinsic viscosity in tetrahydro-naphthalene at 135° C. (I.V.) equal to 1.7 dl/g.

EXAMPLE 2

Preparation of the solid catalyst component

The procedure and ingredients of Example 1 are repeated, but in this case an equimolar quantity of diisobutyl phthalate instead of 1,3-bis(dimethylamino)-2,2-dimethylpropane is used.

The analysis of the solid component shows that it contains, by weight, 19% Mg, 2.7% Ti, and 8.6% ester.

Propylene polymerization

The procedure and ingredients of Example 1 are repeated, but in this case 1.4 moles of 1,3-bis(dimethylamino)-2,2-dimethylpropane instead of cyclohexylmethyldimethoxysilane are used.

120 g of polymer are obtained (corresponding to a yield of 6000 g/gCat), said polymer having an X.I. of 90.1%, and an I.V. equal to 1.7 dl/g.

EXAMPLE 3

PREPARATION OF 1,3-BIS(DIMETHYLAMINO)-2,2-DIPHENYLPROPANE a) Preparation of the 2,2-diphenyl-3-dimethylamino-propionitrile.

Into a 500 ml stainless steel autoclave are introduced 38 g of diphenylacetonitrile (0.197 moles) in 178 ml of a 33% solution of dimethylamine in absolute ethanol.

After having cooled the autoclave, 69 ml of an aqueous formaldehyde 40% solution are slowly added to the content, which is then heated by reflux under magnetic agitation for two days.

The reaction mixture is cooled and poured into 1 liter of water containing 80 ml of concentrated HCl cooled at 0° C. The insoluble material is filtered in acid ambient, and is basified with a soda solution at 20% cooling it with ice.

The oil that is separated is extracted with ether and anhydrated on $Na_2SO_4$. The residual obtained after evaporation of the solvent is distilled under vacuum. The product distills at 145°–147° C. at a pressure of 0.3 mm Hg.

27.3 g of a straw-colored oil which solidifies slowly are recovered (yield=55%).

The recrystallization of a sample from pentane gives some color-free prisms with a melt point=44°–45° C.

$^1$H-NMR (CDCl$_3$):

δ (in ppm):

2.2 (s, 6H, CH$_3$N)

3.3 (s, 2H, CH$_2$N)

7.2–7.5 (m, 10H, phenyls)

b) Preparation of 2,2-diphenyl-3-dimethylaminopropylamine

Into a 1 liter flask equipped with mechanical agitator, refrigerating device, feed funnel, thermometer and pipe for the introduction of nitrogen, are introduced in nitrogen flow 7.5 g of LiAlH$_4$ (0.198 moles) in 175 ml of anhydrous ethyl ether. The content is cooled with an ice and water bath in order to maintain the temperature below 5° C., then 24.7 g of 2,2-diphenyl-3-dimethylaminopropionitrile (0.0988 moles) prepared above is dissolved in 150 ml of anhydrous ethyl ether are added dropwise in one and half hour.

The content is agitated for one and half hour maintaining the temperature below 5° C. The reaction mixture is slowly poured into an ice and water bath, and then the Al salts are filtered.

The filtrate is washed with ether, and the ether phase is extracted with an excess of diluted HCl. The acid extract is rendered alkaline with an excess of soda at 20%, and the resulting oil is reextracted with ether. The product is anhydrated on Na$_2$SO$_4$ and distilled under vacuum. Said product boils at 126°–128° C. at a pressure of 0.2 mm Hg.

22.4 g of 2,2-diphenyl-3-dimethylaminopropylamine are recovered (yield=89%), the product solidifies slowly and completely.

It is recrystallized from pentane and cubes having a melt point=37°–39° C. are obtained.

$^1$H-NMR (CDCl$_3$):

δ (in ppm):

0.85 (wide band, 2H, NH$_2$)

1.9 (s, 6H, CH$_3$N)

3.2 (s, 2H, CH$_2$N)

3.5 (s, 2H, CH$_2$NH$_2$)

7–7.4 (m, 10H, phenyls)

c) Preparation of 1,3-bis(dimethylamino)-2,2-diphenylpropane

Into a 1 liter flask equipped with a mechanical agitator, refrigerating device, drip funnel, and thermometer, are introduced: 34.7 g of 2,2-diphenyl-3-dimethylaminopropylamine (0.137 moles) prepared above, 500 ml of acetonitrile; 76 g of NaBH$_3$CN (1.2 moles).

Then, 55 ml of 37% formaldehyde (2 moles) are dropped in; from time to time some acetic acid is added in order to keep neutral the reaction pH. The reaction is exothermic and the resulting product is a gummy white precipitate.

The solvent is evaporated, 250 ml of a solution consisting of 2N of KOH is added, and it is extracted with ether.

The ether extracts are washed with 50 ml of a 0.5N of KOH solution, and then extracted with HCl 1N; it is neutralized with solid KOH, reextracted with ether, and anhydrated on K$_2$CO$_3$.

The product obtained is purified by column flash chromatography (eluant used: 98 hexane/2 triethylamine).

28.5 g of a white crystalline solid are recovered (yield= 74%).

$^1$H-NMR (CDCl$_3$):

δ (in ppm):

1.9 (s, 12H, CH$_3$N)

3.2 (s, 4H, CH$_2$N)

7.1–7.3 (m, 10H, phenyls)

Preparation of the solid catalyst component

The procedure and ingredients of Example 1 are repeated, but in this case 1,3-bis(dimethylamino)-2,2-diphenylpropane instead of 1,3-bis(dimethylamino)-2,2-dimethylpropane in equimolar quantity is used.

The analysis of the solid component shows that it contains, by weight, 14.1% Mg, 8% Ti, and 5.5% diamine.

Propylene Polymerization

The procedure and ingredients of Example 1 are repeated and 200 g of polymer are obtained (corresponding to a yield of 10,000 g/gCat), said polymer having an X.I. of 90.1%, and an I.V. of 1.7 dl/g.

EXAMPLE 4

Propylene Polymerization

In the polymerization the procedure and ingredients of Example 1 are repeated, but in this case the solid catalyst component of Example 2 and 1.4 mmoles of 1,3-bis(dimethylamino)-2,2-diphenylpropane instead of cyclohexylmethyldimethoxysilane are used.

210 g of polymer are obtained (corresponding to a yield of 10,500 g/gCat), said polymer having an X.I. of 90%, and an I.V. of 1.8 dl/g.

EXAMPLE 5

Preparation of a blend consisting of (II) 1,3 -bis(dimethylamino)-2,2-dicyclohexylpropane (60% in moles) and (III) 1,3-bis(dimethylamino)-2-cyclohexyl-2(1-cyclohexenyl-)propane (40% in moles).

Into a 250 ml steel autoclave are introduced: 200 ml of absolute ethanol; 2.47 g of 1,3-bis(dimethylamino)-2,2 -diphenylpropane (8.76 $10^{-3}$ moles; 150 mg of $RuO_2$ (catalyst).

A few drops of acetic acid are added, the content is fed at ambient temperature at 80 atm of hydrogen, and it is heated to 90° C., while agitating, for about 24 hours. It is then cooled and discharged; the catalyst is filtered, the ethanol evaporated, and the content is basified with soda.

It is extracted with ether (3 times) and anhydrated on $Na_2SO_4$. 2.5 g of product are recovered. The N.M.R. spectra ($^1H$, $^{13}C$ and DEPT) show that said product is a blend of (II) and (III) diamines.

$^1$H-NMR ($CCl_4$):

δ (in ppm):

1–1.84 (m, cyclohexanes)

2 (m, allyl $CH_2$)

2.14 [s, $CH_2N$ of (II)]

2.2 [s, 12H, $CH_3N$, 2 basically coincidental signals for (II) and (III)]

2.44 [dd, $CH_2N$ of (III)]

5.32 (m, vinyl CH)

from the value of the integrals of the signals corresponding to the $CH_2N$ of (II) and (III) one derives the ratio between the latter, which is (II): (III)=60:40)

$^{13}$C-NMR ($CDCl_3$):

δ (in ppm):

22.4 and 23.35 (homoallyl $CH_2$)

25.87 and 26.99 (allyl $CH_2$)

27.3–28.48 ($CH_2$ cyclohexane rings)

41.82 and 42.23 (CH of cyclohexane rings)

46.3 (C quaternary)

48.17 and 48.96 [$CH_3N$, 2 different signals for (II) and (III)]

61.13 and 62.2 ($CH_2N$)

121.95 (vinyl CH)

139.5 (olefin C, s)

$^{13}$C-DEPT ($CDCl_3$)

the $CH_2$ groups give negative signals, and they are:

22.4 and 23.35 (homoallyl $CH_2$)

25.87 and 26.99 (allyl $CH_2$)

27.3–28.49 ($CH_2$ cyclohexane rings)

61.13 and 62.2 ($CH_2N$)

the $CH_3$ and CH groups give positive signals, and they are:

41.82 and 42.23 (cyclohexane CH)

48.17 and 48.96 ($CH_3N$)

121.95 (vinyl CH)

The signals corresponding to 46.3 and 139.5 ppm pertaining to quaternary carbon atoms disappear.

Propylene polymerization

In the polymerization the procedure and ingredients of Example 1 are repeated, but in this case the solid catalyst component of Example 2 and 1.4 mmoles of the above diamine blend instead of cyclohexylmethyldimethoxysilane are used.

116 g of polymer are obtained (corresponding to a yield of 5800 g/gCat) said polymer having an X.I. of 90.3% and an I.V. of 1.7 dl/g.

Comparative Example 1

The procedure and ingredients of Example 1 are repeated, but in this case 2,2,6,6-tetramethylpiperidine in equimolar substitution of 1,3-bis(dimethylamino)-2,2-dimethylpropane is used in the preparation of the solid catalyst component.

60 g of polymer are obtained (corresponding to a yield of 3000 g/gCat), said polymer having an X.I. of 71.9%, and an I.V. of 1.5 dl/g.

Comparative Example 2

The procedure and ingredients of Example 1 are repeated, but in this case 1,4-bis(dimethylamino)-butane in equimolar substitution of 1,3-bis(dimethylamino)-2,2-dimethylpropane is used in the preparation of the solid catalyst component. Traces of polymer are obtained.

Other features, advantages and embodiments of the invention disclosed herein will be readily apparent to those exercising ordinary skill after reading the foregoing disclosure.

In this regard, while specific embodiments of the invention have been described in considerable detail, variations and modifications of these embodiments can be effected without departing from the spirit and scope of the invention as described and claimed.

We claim:

1. A catalyst component for the polymerization of olefins, comprising a magnesium halide in active form, and, supported thereon, a titanium halide or titanium halogen alcoholate and diamine of formula

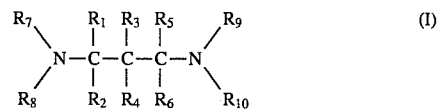

wherein the radicals $R_1$ to $R_{10}$ are the same or different and are hydrogen, $C_1$–$C_{18}$ linear or branched alkyl radicals, $C_3$–$C_{18}$ cycloalkyl radicals, $C_6$–$C_{18}$ aryl radicals, $C_7$–$C_{18}$ alkaryl or aralkyl radicals, with the proviso that at least one of the $R_7$ and $R_8$ radicals and at least one of the $R_9$ and $R_{10}$ radicals are not hydrogen, and wherein at least one of the $R_3$ and $R_4$ radicals is selected from the group consisting of methyl, ethyl, n-propyl, isopropyl, n-butyl, isobutyl, sec-butyl, tert-butyl, cyclohexyl, cyclohexenyl, cyclohexylmethyl, phenyl and benzyl.

2. The catalyst component of claim 1, wherein the radicals $R_1$, $R_2$, $R_5$ and $R_6$ are selected from the group consisting of hydrogen, methyl, ethyl, n-propyl, isopropyl, n-butyl, isobutyl, sec-butyl, tert-butyl, cyclohexyl, cyclohexenyl, cyclohexylmethyl, phenyl and benzyl.

3. The catalyst component of claim 1, wherein the radicals $R_7$ to $R_{10}$ are selected from the group consisting of $C_1$–$C_6$ alkyls and $C_3$–$C_6$ cycloalkyls.

4. The catalyst component of claim 1, wherein the magnesium halide is $MgCl_2$ and the titanium halide is $TiCl_4$.

5. A catalyst for the polymerization of olefins comprising the reaction product of:

A) a catalyst component as defined in claim 1;

B) an Al-alkyl compound; and optionally

C) an electron donor compound.

6. The catalyst of claim 5, wherein the Al-alkyl compound (B) is an Al-trialkyl compound.

7. The catalyst of claim 5, wherein the electron-donor compound (C) is selected from the compounds of formula:

$$R_mSiY_nX_p$$

wherein:

R is a $C_1$–$C_{20}$ alkyl, $C_2$–$C_{20}$ alkenyl, $C_6$–$C_{20}$ aryl, $C_7$–$C_{20}$ aralkyl, or $C_3$–$C_{20}$ cycloalkyl;

Y is an —OR', —OCOR', —NR'$_2$ radical wherein R' is the same or different from R and has the same meaning as R;

X is a halogen or hydrogen atom or an —OCOR" or —NR"$_2$ group, wherein R" is the same or different from R', and has the same meaning as R'; m is a number from 0 to 3, n is a number from 1 to 4, p is a number from 0 to 1 and m+n+p is equal to 4.

8. A catalyst for the polymerization of olefins comprising the product of the reaction of an Al-alkyl compound and a diamine of the formula of claim 1 with a solid component comprising a magnesium halide in active form, a titanium halide or titanium halogen alcoholate, and an electron-donor compound extractable with Al-triethyl for at least 70% in moles under standard extraction conditions, said solid component having a surface area greater than 20 m$^2$/g after extraction.

9. The catalyst of claim 8 wherein the electron-donor compound present in the solid component is a phthalic acid ester.

* * * * *